United States Patent
Smiley et al.

(10) Patent No.: US 6,573,307 B1
(45) Date of Patent: Jun. 3, 2003

(54) PROCESS FOR MAKING FLUORINATED POLYMER ADSORBENT PARTICLES

(75) Inventors: Leonard H. Smiley, Philadelphia, PA (US); Christopher Lowe, Cambs (GB); Julie Tucker, Kent (GB)

(73) Assignee: Prometic Biosciences, Inc., Montreal (CA)

( * ) Notice: Subject to any disclaimer, the term of this patent is extended or adjusted under 35 U.S.C. 154(b) by 0 days.

(21) Appl. No.: 09/980,901

(22) PCT Filed: Jun. 12, 2000

(86) PCT No.: PCT/CA00/00701

§ 371 (c)(1),
(2), (4) Date: Apr. 15, 2002

(87) PCT Pub. No.: WO00/77081

PCT Pub. Date: Dec. 21, 2001

Related U.S. Application Data

(63) Continuation of application No. 09/329,289, filed on Jun. 10, 1999.
(60) Provisional application No. 60/088,940, filed on Jun. 11, 1998.

(51) Int. Cl.$^7$ ................................. C08J 9/26; C08J 9/28

(52) U.S. Cl. ............................. 521/64; 264/41; 264/42; 521/150

(58) Field of Search ..................... 521/64, 150; 264/41, 264/42

(56) References Cited

U.S. PATENT DOCUMENTS

| | | |
|---|---|---|
| 3,985,632 A | 10/1976 | Rembaum et al. |
| 4,035,316 A | 7/1977 | Yen et al. |
| 5,607,467 A | 3/1997 | Froix |

*Primary Examiner*—Morton Foelak
(74) *Attorney, Agent, or Firm*—Fish & Richardson P.C.

(57) ABSTRACT

A process to make particles by anaerobic reaction of a water-insoluble solution of organic compounds comprising (a) a monomer selected from $C_{2-4}$ alkylene glycol esters of a $C_{3-6}$ acrylic acid and a divinyl benzene; (b) a polyfluorinated vinyl monomer; (c) a monomer selected from acrylic acid, methacrylic acid and esters thereof; (d) a free radical initiator; and (e) a water-insoluble, organic solvent-soluble porogenic material, the weight ratio of comonomers (a) plus (b) plus (c) to the porogenic material being from 0.5:1 to 2:1. The adsorbent particles produced by the process are useful in carrying out chromatographic separations, or in the production of medical devices.

10 Claims, No Drawings

PROCESS FOR MAKING FLUORINATED POLYMER ADSORBENT PARTICLES

This application is a 371 of PCT/CA00/00701 Jun. 12, 2000 which a continuation of Ser. No. 09/329,289 Jun. 10, 1999 which claims benefit of No. 60/088,940 Jun. 11, 1998.

FIELD OF INVENTION

The invention relates to a process for making fluorinated polymer adsorbent particles and to their use as a stationary phase for carrying out chromatographic separations.

BACKGROUND OF THE INVENTION

Support materials for use in high productivity liquid chromatography must be mechanically strong in order to withstand operation at high rates of flow under high pressures. Moreover, they must be stable over the wide range of pH to which such materials are subjected during normal operation and regeneration. The stability of the polymeric particles in its environment allows it to withstand degradation and decomposition. Physical properties of particular importance to chromatographic media are (1) sphericity of the particles; (2) high surface area; (3) high pore volume and availability; (4) wide range of pore diameters; and (5) wide range of particle diameters.

The particles of the invention are an improvement over known particles in respect of many of the above properties. Furthermore, the fluorinated surface of certain of the particles of the invention present unusual and unexpected polarity that is beneficial in performing chromatographic separations such as that used for DNA.

SUMMARY OF THE INVENTION

The invention is therefore directed to the manufacture of improved fluorinated particles having adsorbent properties for superior performance as the stationary phase for use in chromatographic separations.

The invention provides a process for the preparation of porous spherical particles of fluorinated polymer adsorbent comprising the steps of:

(1) forming a water-insoluble solution of organic compounds comprising a monomer selected from $C_{2-4}$ alkylene glycol esters of a $C_{3-6}$ acrylic acid or divinyl benzene; a polyfluorinated vinyl monomer; a free radical initiator; and a water-insoluble, organic solvent-soluble porogenic material, the weight ratio of the comonomers to porogenic material being from 0.5:1 to 2:1;

(2) forming a dilute solution of a dispersing agent in water from which any oxygen has been purged with inert gas;

(3) with agitation and inert gas purging, rapidly dispersing the water-insoluble solution of organic compounds from step (1) into the dilute aqueous solution from step (2) and, as necessary, adjusting the temperature of the dispersion to 30–90° C. to initiate copolymerization of the monomers, the level of mixing energy being sufficient to disperse the water-insoluble solution of organic compounds in the solution from step (2) in the form of liquid droplets having an average diameter of no more than 10–300 micrometers, at least 90% of the droplets being within 40% above or below the average mean particle diameter;

(4) continuing the agitation and oxygen purging of the dispersion from step (3) for a time sufficient to effect complete copolymerization of the monomers and particulation of the droplets in the form of finely divided polymer particles by precipitation of the copolymer therein;

(5) separating the finely divided copolymer particles from the polymerization reaction medium;

(6) extracting the porogenic material from the separated copolymer particles of step (5) by washing the particles with inert organic solvent, thereby forming pores within the copolymer; and (7) drying the porous copolymer particles.

The invention further provides a process for the preparation of porous spherical particles of fluorinated polymer adsorbent comprising the steps:

(1) forming a water-insoluble solution of organic compounds comprising (a) a monomer selected from $C_{2-4}$ alkylene glycol esters of a $C_{3-6}$ acrylic acid and a divinyl benzene; (b) a polyfluorinated vinyl monomer; (c) a monomer selected from acrylic acid, methacrylic acid and esters thereof; (d) a free radical initiator; and (e) a water-insoluble, organic solvent-soluble porogenic material, the weight ratio of comonomers (a) plus (b) plus (c) to the porogenic material being from 0.5:1 to 2:1;

(2) forming a dilute solution of a dispersing agent in water from which any oxygen has been purged with inert gas;

(3) with agitation and inert gas purging rapidly dispersing the water-insoluble solution of organic compounds from step (1) into the dilute aqueous solution from step (2) and, as necessary, adjusting the temperature of the dispersion to 30–90° C. to initiate copolymerization of the monomers, the level of mixing energy being sufficient to disperse the water-insoluble solution of organic compounds in the solution from step (2) in the form of liquid droplets having an average diameter of no more than 10–300 micrometers, at least 90% of the droplets being within 40% above or below the average mean particle diameter;

(4) continuing the agitation and oxygen purging of the dispersion from step (3) for a time sufficient to effect complete copolymerization of the monomers and particulation of the droplets in the form of finely divided polymer particles by precipitation of the copolymer therein;

(5) separating the finely divided copolymer particles from the polymerization reaction medium;

(6) extracting the porogenic material from the separated copolymer particles of step (5) by washing the particles with inert organic solvent, thereby forming pores within the copolymer; and (7) drying the porous copolymer particles.

The invention further provides adsorbent particles made by the process described above.

The present invention further provides uses for the particles according to the invention as a stationary phase in chromatographic techniques. Certain particles of the invention are particularly suited to use where the sample to be chromatographed is a macromolecule containing nucleotides, nucleosides or polypeptides, such as DNA, RNA or endotoxins.

DETAILED DESCRIPTION OF THE INVENTION

The invention relates to a method for making high quality adsorbent fluoropolymer particles by suspension polymerization with an aqueous solution containing a conventional dispersing agent. The basic components of the process are (1) the water-insoluble polymerization system, which is comprised mainly of a polyfluorinated monomer, two or more ethylenically unsaturated monomers and a free radical-initiating catalyst, and (2) the dispersion medium, which is a dilute aqueous solution containing a conventional dispersing agent. By water-insoluble solution, it is meant a solution sufficiently water-insoluble to permit suspension polymerization to occur. Preferred ethylenically unsaturated monomers are monomers having divinyl functionality. Non-fluorinated monomers having divinyl functionality are more preferred. Poly(vinyl alcohol) and poly(vinyl pyrrolidone) are preferred dispersing agents

A. Dispersing Agents

The polymerization of the polyfluorinated copolymer for use in the invention is conducted in the presence of a dilute aqueous solution containing a dispersing agent, for example poly(vinyl alcohol) or poly(vinyl pyrrolidone). The principal function of the dispersing agent is to adjust the interfacial surface tension between the finely dispersed water-insoluble polymerization components and the continuous aqueous medium phase. By regulating the concentration of dispersing agent dissolved in the aqueous medium, the droplet size of the dispersed polymerization system and thus the size of the resultant polymerized particles can be more finely controlled.

So long as the dispersing agent is essentially completely dissolved in the aqueous medium, a wide range of molecular weights of the dispersing agent may be used successfully in the practice of the invention. One preferred dispersing agent is PVA that is at least 80% hydrolyzed, and more preferably at least 86% hydrolyzed, with a molecular weight of at least about 1,000. The maximum usable molecular weight is a function of the ambient water solubility of the dispersing agent. For example, the molecular weight of the PVA used will ordinarily not exceed 150,000 and preferably is no higher than 100,000.

For the purposes of the invention, the concentration of PVA in the aqueous medium should be within the range of 1 to 50 mL PVA per liter of water. Below 1 mL/L the modifying effect of the PVA is insufficient and above about 50 mL/L no further advantage is discernible. It is, of course, desirable to use lesser amounts of PVA in order to avoid energy-wasting increases in viscosity of the aqueous medium.

B. Polymerization System

1. Polyfluorinated Monomer: As set out above, the fluorine-containing comonomer must contain a plurality of fluorine (F) substituents. It is preferred that the fluorinated comonomer contains at least three F substitutions. In addition to these restrictions on its degree of fluorination, it is essential that the fluorinated comonomer be essentially completely insoluble in water under the polymerization temperatures encountered and essentially completely soluble in the other components of the dispersed polymerization system.

Suitable polyfluorinated comonomers are those containing active vinyl sites such as acrylates, methacrylates, vinyl compounds, maleates and itaconates. Among the many compounds within those categories are pentafluorostyrene, bis-hexafluoroisopropyl itaconate, bis-hexafluoroisopropyl maleate, heptadecafluorodecyl acrylate, perfluorooctyl methacrylate, 2,2,3,3-tetrafluoropropyl methacrylate, monotrifluoroethyl itaconate, 2,2,2-trifluoroethyl maleate, vinyl benzyl perfluoroctanoate and vinyl trifluoroacetate.

2. Vinyl Comonomers: It is preferred that the comonomer component of the polyfluorinated copolymer for use in the invention be a non-fluorinated $C_{2-4}$ alkylene glycol ester of a $C_{3-6}$ acrylic acid (the cross-linking comonomer). The cross-linking comonomer must have at least two vinyl groups. Suitable comonomers having this composition are ethyleneglycol dimethacrylate, 1,3-propyleneglycol dimethacrylate, 1,4-butanediol dimethacrylate, ethyleneglycol itaconate, ethyleneglycol diacrylate, and ethyleneglycol dimaleate. Divinyl benzene can also be used for this purpose.

A mixture of non-fluorinated comonomers can also be used, where one non-fluorinated comonomer has at least two vinyl groups, i.e. the cross-linking comonomer, and the third monomer, i.e. co-monomer (c), is acrylic acid, methacrylic acid, or an ester of acrylic or methacrylic acid. Typical esters are the methyl, ethyl, and hydroxyethyl esters of these acids, epoxide containing esters of these acids and amine esters of these acids. Thus, a forth co-monomers selected from co-monomers (c) may be used in the synthesis.

The presence of co-monomer (c) facilitates the attachment of ligands for use in chromatographic separations by obviating the use of PVA as a linker, as described in U.S. Pat. Nos. 5,773,587 and 6,046,246, between the perfluorinated particle and the ligand. The addition of monomer (c) has little effect on the properties of the improved particles of the invention, such as stability of the particle or pore size.

We have shown that between 1 and 30% of the cross-linker ethylene glycol dimethacrylate can be replaced with a third or forth monomer selected from co-monomers (c). These co-monomers can be chosen depending on the functionality desired. For example, functional esters of acrylic and methacrylic acid can be added such as those containing hydroxyl, epoxide, amine, quarternary ammonium, sulphonic acid etc. can be used.

3. Free Radical Initiator: An essential component of the polymerization is a source of free radicals. In particular, the system must contain one or more compounds that thermally decompose under the conditions of polymerization to form free radical species. A preferred free radical agent is a mixture of azo-bis-isobutyronitrile (AIBN) and benzoyl peroxide (BPO). From about 10 to about 50 mg/L are needed for this purpose. It is recognized that higher concentrations are operable functionally. However, it is preferred to use as small amounts as possible in order to lessen the amount of extraneous materials in the formed polymer particles.

C. Porogen

Suitable porogenic materials are those organic compounds which are (1) chemically inert with respect to the other components of the polymerization phase, (2) completely soluble in the polymerization system, (3) completely insoluble in the continuous aqueous phase and (4) readily extractable from the polymerized particles at relatively low temperatures with a low molecular weight organic solvent. Dibutyl phthalate, which is easily removed by washing the polymer particles with dichloromethane, is a preferred porogen for use in the invention. Other suitable porogens include toluene, isopropyl benzene, 2-methyl-4-pentanone, 2-methyl-4-pentanol and chlorobenzene.

D. Polymerization Procedure

The polymerization should be conducted in the essentially complete absence of air or any other source of oxygen contamination, which might lead to adverse reactions with any of the components of the polymerization system, especially the monomers, crosslinking agent and free radical initiator. It has been found that the most practical way of removing and preventing the introduction of oxygen into the polymerization system is continuously to purge the polymerization reaction system before, during, and after completion of the polymerization process with an inert gas. Any of the inert gases are, of course, suitable for this purpose. However, argon and nitrogen are the least expensive and will be preferred in most instances. Because the polymerization is conducted under very high energy mixing conditions, the method of introducing the purging gas is not particularly critical, so long as it is adequate in volume.

The dispersing agent functions principally for more precise control of interfacial tension between the dispersed monomer droplets and the aqueous continuous medium. The droplet size is controlled more dominantly by the amount of mixing energy used to disperse the polymerization system. Thus, only comparatively low concentrations of PVA as dispersing agent are required in the aqueous medium, e.g., on the order of 1–100 g/L. A PVA concentration within the range of 0.5–40 g/L is preferred. Though higher concentrations can be used, they do not improve functionality. Because of the necessity of forming very small droplets during the polymerization, it is, of course, desirable to avoid higher PVA concentrations which would render the aqueous medium more viscous.

The amount of energy input into the polymerization is primarily a function of the polymer particle size that is desired. Thus, if larger particles are sought, the degree of mixing (energy input) is lowered. If smaller particles are sought, the degree of mixing is raised. It is preferred that droplet size during polymerization be controlled to obtain polymer particles within the range of 5–300 micrometers, 20–100 micrometers being especially preferred.

F. Particle Properties

Ideal chromatography media need to have the following properties: (1) spherical shape; (2) high surface area; availability of a wide range of (3) pore diameters and (4) particle diameters; (5) high pore volume; (6) high mechanical strength; and (7) both chemical and mechanical stability throughout the pH range to which the media are exposed in use.

Sphericity of the particles, rather than irregular, granular shapes, is advantageous for providing minimum resistance to flow through a packed bed of the particles and minimum backpressure. Such regularly shaped particles are less likely to undergo densification during use.

Particle size and size distribution are also important properties of the particles of the invention. In general, particles larger than about 20 micrometers facilitate lower backpressure in packed columns. Moreover, the chromatographic peak width and peak shape obtained with larger particles are usually wider than the peak width and shape obtained with particles in the range of 3–15 micrometers. Narrow peak shapes are frequently desired for many types of separations.

The available surface area of polyfluorinated particles produced by the method of the invention is ordinarily preferred to be at least about 200 $m^2/g$ in order to obtain higher loading of antigens on the particulate media. Nevertheless, media having much lower surface areas can readily be made according to the invention by changing the amount of porogen used in the polymerization system and decreasing the size of the particles. Concomitantly, a large pore volume of at least 0.5 mL/g is needed in order to obtain a high surface area.

A wide range of pore sizes must be available for different chromatographic procedures. Large pores are needed for the efficient capture of larger molecules, such as proteins, while small pores are needed for the efficient capture of small molecules. In general, the range of pore sizes may extend from below 60 Å to as high as 1,000 Å, 300–800 Å being preferred. This range of sizes is quite readily available using the invention method of adjusting the relative amount and type of porogen within the formed polymer particles.

Because of the wide range of pH values at which chromatography media are used and because of the very high pH ranges that are encountered frequently to clean and regenerate them, it is necessary that they be chemically inert throughout the entire range of such pH exposures. In particular, chromatographic media must be able to withstand the high pH (12 or higher) encountered by the use of NaOH for cleaning the media particles, typically 0.1–1 normal.

G. Uses of the Particles

The adsorbent particles of the invention are quite versatile and may be used as the stationary phase for carrying out a wide variety of chromatographic separations. Examples of the chromatographic separations contemplated include reverse phase separations, affinity separations, expanded bed separations, ion-exchange chromatography, gel filtration, chromatographic component separation, solid phase extraction, filtration and other recognised technical methods of distinguishing, measuring or collecting components of a chemical, biological or physical mixture. The particles may be used as support for grafting different types of ligands. Certain of the particles are particularly suited to use where the sample to be chromatographed is DNA, RNA or polypeptides.

The polyfluorinated particles of the invention can be used for chromatographic separations either with or without a coating of a hydrophilic polymer, such as poly(vinyl alcohol).

The surface of the uncoated particles of Examples 3 and 4 is hydrophobic, but with a slight polarity, which combination of properties is ideal for reverse phase chromatographic separations. Reverse phase chromatography involves the use of a relatively non-polar stationary phase in conjunction with a very polar mobile phase that is usually water. This technique is used to separate solutes of lower polarity. Reverse phase chromatography is usually performed using silica that is coated with an organic silane to provide hydrophobicity. However, the hydrophobized silica has a severe limitation in that it cannot be used at pH greater than 11 and cannot be cleaned with concentrated caustic soda solutions without dissolving the particles. A substantial advantage of the polyfluorinated particles of the invention is that they do not have this limitation.

The use of the uncoated invention particles for reverse phase chromatography is illustrated by Example 28 and the stability of the particles of the invention toward basic solutions is shown by the data obtained in Example 29 below.

Suitable hydrophilic polymers for use in coating the polyfluorinated particles of the invention are those which are uncharged, water-soluble, non-cyclic and have a multiplicity of hydroxyl groups. Though many several such hydrophilic polymers are useful for this particular function, (polyvinyl alcohol) is preferred.

Advantageously, the polyfluorinated compounds of the invention may be used in medical devices with or without ligands on their surfaces to do separations that are not classified as chromatographic. For example, components of blood can be separated using a medical device in which the blood is pumped through a cartridge extra-corporeally and returned to the body. A component such as a toxin would be removed and not returned to the body.

Due to the stability of the polyfluorinated particles of the invention, sterilization can be done by gamma irradiation without destroying the particle. This property makes the particles particularly well suited for uses in medical devices that must be sanitized.

E. Derivatization of Particles

If desired, the PVA-coated polyfluorinated particles of Examples 5 and 6 can be functionalized by reacting suitable molecules with the hydroxyl groups of the PVA. Thus, strong cationic ion exchange functionality can be provided to the particle surfaces by placing sulfonic acid groups on the surface. Likewise, strong anionic ion exchange functionality can be provided by applying quaternary amines. Weak cation functionality can be produced by the use of carboxylic groups and weak anion functionality can be obtained by the use of primary amines.

EXAMPLES

Example 1

Production of a Porous Copolymer of Ethyleneglycol Dimethacrylate, Pentafluorostyrene and Hydroxyethylmethacrylate Four hundred ninety mL of distilled water were placed in a vessel and agitated with a high efficiency paddle mixer at 800 rpm. With continuing agitation, argon gas was added to purge oxygen from the water and 3.9 g of poly(vinyl alcohol) were added to the water. Agitation and purging were continued for 30 minutes, during which vortexing of the mixture was reduced by changing the angle of the agitator. Ethyleneglycol dimethacrylate (50.1 g) and pentafluorostyrene (39.8 g) and hydroxyethyl methacrylate (5.6 g) were mixed together and 127 mL of dibutylphthalate were added to the mixture after which 0.48 g azo-bis-isobutyronitrile (AIBN) and 0.45 g of benzoyl peroxide (BPI) were added. The mixture was then stirred until homogeneous. The homogeneous mixture was then added rapidly to the aqueous poly(vinyl alcohol) solution and the resultant polymerization mixture was heated to about 80° C. Agitation at 800 rpm and argon purging were continued throughout until the polymerization was complete.

Upon separating the formed fluoropolymer particles from the polymerization medium, they were washed sequentially with (1) 200 mL of distilled water at 60° C., (2) 200 mL of acetone at 60° C. and (3) 200 mL of a 30/70% by volume mixture of hot water and acetone at 70° C. Upon completion of the washing steps, the particles were dried overnight in an oven at 70° C.

The washed and dried fluoropolymer particles were then refluxed with 10% wt. dichloromethane for 6–7 hours at 50° C. to remove the porogenic material from the particles. The porogen-free particles were placed on a sintered glass funnel and rinsed with 50 mL of acetone per gram of particles, after which the rinsed particles were dried overnight at 70° C.

The washed polyfluorinated particles had an average particle size of 51 micrometers, surface area of 300 m$^2$/g and pore volume of 1.0 mL/g. This procedure was very effective in making porous, spherical beads that would withstand pressure of 2000 psi in a chromatographic separation.

Variations of this Example were also performed, as follows. A porous copolymer of ethylene glycol dimethacrylate and pentafluorostyrene and epoxy ethyl methacrylate was prepared by adding to 490 ml of distilled water nitrogen gas over a 30-minute period to purge the oxygen from the water. Polyvinyl alcohol (3.9 g) was added. Pentafluorostyrene (30.9 g), divinylbenzene (35.7 g), epoxyethyl methacrylate (20.0 g) and dibutyl phthalate (127 ml) were mixed together in a separate vessel. Azo-bis-isobutyronitrile (0.40 g) and benzoyl peroxide (0.30 g) were added to the mixed monomers. The mixture of the monomers and the peroxide catalysts was added to a stirred mixture of the water and PVA. The mixture was heated to 80 C. with agitation of 800 rpm from a motor-driven, stirring paddle. The mixture was allowed to polymerize over a 4-hour period after which the polymerization was considered complete. The polymer particles were separated from the water and washed and dried. The porogen was removed as described above.

The polymerization was conducted as in Example 1 only poly(vinyl pyrrolidone) was substituted for the PVA dispersing agent. The polymerization proceeded as in Example 1, only the particles were more finely divided after drying. In Example 1, the particles often clumped together on drying but were easily broken apart by mechanical or ultrasonic methods. The use of poly(vinyl pyrrolidone) prevented the clumping.

Porous, perfluorinated, ion-exchange particles can also be made by substituting a functional co-monomer for the crosslinker, ethylene glycol dimethacrylate. An example is the substitution of 20.0 g. of methacrylic acid for the ethylene glycol dimethacrylate. The resulting polymer can function as a weak cation exchanger.

Example 2

Production of a Porous Copolymer of Ethyleneglycol Dimethacrylate, 2-(N-ethyl Perfluoro Octane Sulfo Amido) Perfluoromethacrylate and Methacrylic Acid A porous copolymer of ethyleneglycol dimethacrylate, 2-(N-ethyl perfluoro octane sulfo amido) perfluoromethacrylate and methacrylic acid was prepared in the following manner:

Set-up:

1 L. cylindrical reactor fitted with a "type E" agitator (Cole Palmer, 6 cm diameter and 10 cm height), reflux condenser, gas inlet tube and immersed temperature probe. The agitator is positioned so that its top impeller blade is located just above the level of the aqueous phase.

Aqueous phase:

3.9 g PVA (Aldrich, 85,000 to 146,000 Daltons, 97–99% hydrolyzed) in 490 mL deionized (DI) water Organic phase:

1.7 g of polystyrene (Aldrich, 90,000 MW standard)

171 mL isopropyl benzene (Aldrich, 99%)

68.5 g ethylene glycol dimethacrylate (Aldrich, 98%, 100 ppm methyl ether of hydroquinone (MEHQ)

85.6 g 2-(N-ethylperfluorooctane sulphonamido) ethyl methacrylate (Monomers, Polymers and Dajack)

17.1 g of methacrylic acid 0.57 g AIBN (Aldrich, 99%)

1.14 g BPO (Aldrich, 98%)

The aqueous phase was prepared by predissolving the PVA in water at approximately 50° C. The aqueous phase was charged to the reactor and sparged with nitrogen for 25 minutes.

The polystyrene was pre-dissolved in the isopropyl benzene. The mixture of the three monomers was then added, followed by the initiators. After stirring for 1 hour, the organic phase still appeared cloudy and was added as such to the reactor. Under a nitrogen sweep, the mixture was stirred at 800 rpm and heated to 80° C. over a period of 30 minutes. Upon reaching reaction temperature, most of the organic phase agglomerated into a single mass that broke up into individual beads again after 25 minutes.

After 9 hours at reaction temperature, the system was allowed to cool, the aqueous phase siphoned out and the resin beads washed with 500 mL DI water, 500 mL acetone, 500 mL acetone water (30:70), 500 mL hot water and twice with 500 mL acetone.

After air drying, the resin weight is 168 g.

The resin is refluxed for 5 hours in 1 L methylene chloride, washed with 1 L acetone and air dried.

The washed and dried fluoropolymer particles were then refluxed with 10% wt. dichloromethane for 6–7 hours at 50° C. to remove the porogenic material from the particles. The porogen-free particles were placed on a sintered glass funnel and rinsed with 50 mL acetone per gram of particles, after which the rinsed particles were dried overnight at 70° C. The resultant porous beads had a particle size of 50 μm and a surface area of 300 m/gm.

Example 3

Production of a Porous Copolymer of Ethyleneglycol Dimethacrylate and Pentafluorostyrene A porous copolymer of ethyleneglycol dimethacrylate and pentafluorostyrene was prepared according to the procedure described in Example 1, mixing together 55.7 g of ethyleneglycol dimethacrylate and 39.8 g of pentafluorostyrene No ethyl methacrylate was added to the mixture. This procedure was also very effective in making spherical porous particles of pentafluorostyrene.

Example 4

Production of a Porous Copolymer of Ethylene Glycol Dimethacrylate and 2-(N-ethyl Perfluoro Octane Sulfo Amido) Perfluoromethacrylate A porous copolymer of ethylene glycol dimethacrylate and 2-(N-ethyl perfluoro octane sulfo amido) perfluoromethacrylate was prepared according to Example 2, except that the organic phase was composed of:

1.7 g of polystyrene (Aldrich, 90,000 MW standard)
171 mL isopropyl benzene (Aldrich, 99%)
85.6 g ethylene glycol dimethacrylate (Aldrich, 98%,. 100 ppm methyl ether of hydroquinone (MEHQ)
85.6 g 2-(N-ethylperfluorooctane sulphonamido) ethyl methacrylate (Monomers, Polymers and Dajack)
0.57 g AIBN (Aldrich, 99%)
1.14 g BPO (Aldrich, 98%)

The procedure was very effective for making porous spherical particles of perfluoromethacrylate.

Variations of Example 3 and 4 were performed to demonstrate the flexibility of the process in making particles of various pore morphologies, as illustrated in the following table:

| Porogen | % ethylene glycol in pentafluorostyrene mixture | Pore Diameter A | % ethylene glycol in methacrylate mixture | Pore Diameter A |
|---|---|---|---|---|
| Toluene | 50 | 37 | | |
| Toluene | 40 | 122 | | |
| Di-butyl phthalate | 50 | 105 | 50 | 184 |
| Di-butyl phthalate | 40 | 73 | 40 | 261 |
| Di-butyl phthalate | 30 | 78 | | |
| 2-methyl-4-pentane | 50 | 339 | 50 | 46 |

The above table illustrates the effect that the type and amount of the porogen selected may have in different monomer systems.

Example 5

Coating of Styrenic Fluoropolymer Particles with PVA

Using dry fluoropolymer particles prepared in the manner of Example 3, 50 g of such particles were de-agglomerated by sonication in methanol for 5 minutes and soaked overnight in 150 ml of methanol. This de-agglomeration step was carried out in separate batches of 2 g resin in 20 mL methanol.

The methanol resin slurry was placed in a 3 L round bottom flask and enough methanol siphoned out so that it just covered the beads. A solution of 80 g PVA (31,000 to 50,000 Daltons, 98% hydrolyzed) in 1 L deionized water, previously prepared by dissolving the PVA at 50° C., was then added to the flask and the resulting, slurry stirred at room temperature for 24 hours. After collecting a sample for PVA content analysis, the loading solution was separated from the beads by decantation. The beads were transferred to a fritted funnel and washed twice for 10 minutes with 500 mL deionized water, followed by removal of the water by suction. The water washes were combined and a sample retained for PVA content analysis. The washed beads were returned to the round bottom flask, and 1 L of deionized water was added. Stirring was resumed, and 1 mL of 50% aqueous solution of glutaraldehyde was added, immediately followed by 8 mL of 5 N aqueous HCl. After stirring for an additional 24 hours at room temperature, the beads were transferred to a fritted funnel, drained, washed three times with 1 L deionized water and set aside as a wet slurry.

This example shows that spherical polyfluorinated particles made in accordance with the invention can be readily coated with poly(vinyl alcohol) in this manner.

Example 6

Coating of Styrenic Fluoropolymer Particles with PVA

Again using dry fluoropolymer particles prepared in the manner of Example 3, 50 g of the particles were soaked in methanol and coated with PVA in the manner of Example 5, except that the concentration of the PVA in the aqueous solution was raised to 20 g/L.

Example 7

Coating of Methacrylic Fluoropolymer Particles with PVA

In this Example, 50 g of fluoropolymer particle prepared in the manner of Example 4 were coated with PVA in the manner of Example 5.

Example 8

Measurement of PVA Coating on Fluoropolymer Particles

The concentration of PVA was determined by measuring the absorbance of the PVA/iodine/boric acid complex measured at 690 nm and comparing it with a calibration curve prepared using standard PVA solutions. The linear range of the calorimetric assay is up to 1 mg PVA/mL. The amount of PVA adsorbed on the resin was determined by the difference of the initial coating solution concentration minus the final solution concentration. Results are reported in mg or g PVA/g dry resin.

For a 9.31 mg/mL PVA coating solution, dilute samples 100× with distilled water. Pipette 2.0 mL of the samples prepared in 1) into the cuvette along with 0.5 mL of the 0.6M boric acid solution and 0.1 mL of the $KI/I_2$ solution. Mix and let stand in the darkness for 30+5 min. before taking the absorbance rating at 690 nm. Calculate the weight of PVA adsorbed onto the fluoropolymer beads by the following relationship:

$$\text{mg PVA}/\text{g resin} = \frac{(Ci)(Vi) - (Cf)(Vf)}{W}$$

where,
- Ci=Concentration (mg/mL) of initial PVA coating solution
- Vi=Volume (mL) of PVA coating solution
- Cf=Concentration (mg/mL) of PVA coating solution at the end of coating process
- Vf=Final volume (mL) of coating solution
- Vf may be greater than Vi due to a contribution from the wetting solvent
- W=Weight (g) of dry fluoropolymer used in the coating process Using this method, the amount of PVA adsorbed onto the perfluorinated polymers was measured at 0.4 g PVA per g of the dry fluoropolymer prepared as in Example 5 and 1.51 g PVA per g of the dry fluoropolymer prepared as in Example 7.

This example shows that the polyfluorinated polymer of the invention was well coated with poly(vinyl alcohol).

Example 9

Measurement of BSA Capacity of PVA-coated Fluoropolymer Particles

Fluoropolymer prepared and coated with a high level of PVA in the manner of Example 5 was tested with respect to their human serum albumin (HSA) capacity. In particular, 4 mL of a 4 mg/mL solution of HSA in 20 mM phosphate buffer at pH 7.4 were added to 0.5 g of PVA coated beads prepared as in Example 5 and the resulting slurry rotated on a flat bed mixer for 16 hours at room temperature. The concentration of HSA in the supernatant was then determined using the Bradford assay. The amount of protein non-specifically bound to the resin, calculated by difference, was 2 mg/g dry fluoropolymer.

This example shows clearly that protein will bind to the uncoated invention substrate more efficiently than to the corresponding coated substrate.

Example 10

Measurement of HSA Capacity of PVA-coated Fluoropolymer Particles

Fluoropolymer particles prepared and coated with a low level of PVA in the manner of Example 5 were tested with respect to their HSA capacity by the same procedure as Example 9. The amount of HSA adsorbed was determined to be 12.5 mg/g of dry resin.

The example shows that when poly(vinyl alcohol) is coated onto the polyfluorinated particles of the invention, it is a uniform, effective coating.

Example 11

Measurement of Lysozyme Capacity of PVA-coated Fluoropolymer Particles

Fluoropolymer particles prepared and coated with a high level of PVA in the manner of Example 6 were tested with respect to their lysozyme capacity by the same procedure as Example 9. In particular, 4 mL of a 4 mg/mL-solution of lysozyme in 20 mM carbonate buffer at pH 9.0 was added to 0.5 g of PVA coated beads prepared as in Example 6. The resulting slurry was rotated on a flat bed mixer for 16 hours at room temperature. The concentration of lysozyme in the supernatant was then determined based on the supernatant's adsorption at 280 nm. The amount of protein non-specifically bound to the fluoropolymer beads, calculated by difference, was 5 mg/g dry resin.

Example 12

Size Exclusion Chromatography of Proteins

A 10 mL Pharmacia RR 10/30 column was packed with fluoropolymer particles prepared as in Example 5 and equilibrated with 20 nM phosphate buffer at pH 7.0. The column void volume (Vo) was determined by measuring the elution volume (Ve) of Blue Dextran 2000 (0.5 mL injection, 4 mg/mL, 20 mM phosphate buffer at pH 7.0) 0.05 mL of a 10 mg/mL each of ribonuclease A, ovalbumin and aldolase was loaded onto the column and eluted with the equilibration buffer at 0.02 mL/min. Similarly, a solution of chymotrypsinogen A and bovine serum albumin were loaded onto the column and eluted with the equilibration buffer at a flow rate of 0.02 mL/min. The elution volumes of the various proteins were measured from the chromatogram (UV detection) and their respective partition coefficients (Kav) calculated using the following equation:

$$Kav=(Ve-Vo)/(Vt-Vo)$$

where Vt is the total volume of the column.

The results, summarized in Table 1 below, show the expected inverse relationship between partition coefficient and molecular weight for globular proteins.

TABLE 1

| PROTEIN | MOLECULAR WEIGHT (Daltons) | PARTITION COEFFICIENT |
|---|---|---|
| Ribonuclease A | 13,700 | 1 |
| Chymotrypsinogen A | 25,000 | 0.36 |
| Ovalbumin | 43,000 | 0.18 |
| Albumin | 67,000 | 0.13 |
| Aldolase | 158,000 | 0.07 |

Example 13

Binding of Blue Dye to PVA-coated Fluoropolymer Particles

This example was directed to the binding of a blue dye at low concentration on PVA-coated fluoropolymer particles.

To 1 mL of PVA-coated fluoropolymer beads prepared as in Example 5 were added a solution of 50 micromol (40 mg) of Cibacron Blue F3G-A in 8.4 mL of water and 250 microliters of 2M NaCl. After mixing for 30 minutes on a flat bed mixer, 500 micromoles of $Na_2CO_3$ were added and the slurry tumble-mixed for 16 hours at 80° C. The beads were then washed, retaining the filtrates, on a glass sinter with 50 mL each of water, 1 M NaCl, dimethylformamide, water 3% (v/v) methanol/water, water, methanol, water, 1 M NaOH and finally 100 mL fractions of water until the filtrate became clear. The amount of Cibacron Blue F3G-A bound to the resin—15 micromol/mL was determined by measuring the dye concentration in the washing solutions, determined by adsorbance at 620 nm, and calculating the amount bound by difference.

Example 14

Binding of Blue Dye to PVA-coated Fluoropolymer Particles

This example was directed to binding Cibacron Blue F3G-A dye to a PVA-coated styrenic fluoropolymer particles with a high concentration of the blue dye. The resin was coated with the PVA in the manner of Example 6, except that the amount of water to dissolve the So Mmoles of blue dye was 1 mL. The dye was applied in the manner of Example 13. The resulting ligand density was 25 micromoles per mL of the fluoropolymer particles.

Example 15

Lysozyme Capacity of the Affinity Polymer

This example was carried out using a fluoropolymer prepared in the manner of Example 13, which contained a blue dye binding with low ligand density. A 1 mL Pharmacia HR 5/10 column was packed with a resin prepared as in Example 13 and equilibrated with sodium phosphate buffer (20 mM, pH 7.4). 4 mL of a 5 mg/mL solution of lysozyme in the equilibration buffer was loaded onto the resin at 1 mL/min. The lysozyme was then eluted from the resin using 1 M NaCl in 20 mM sodium phosphate buffer, pH 7.4. The amount of lysozyme eluted, as determined by measuring the eluent's absorption at 280 nm, was 18 mg per mL of fluoropolymer.

This example should be compared with Example 11 where no blue dye was bonded to the poly(vinyl alcohol).

Example 16

Lysozyme Capacity of the Affinity Polymer

This example was carried out using a fluoropolymer prepared in the same manner as Example 14, but having a high ligand density. The amount of lysozyme eluted was 20 mg/mL of resin.

Example 17

Non-adsorption of Myoglobin by the Affinity Polymer

A fluoropolymer was prepared using the procedure of Example 14 using myoglobin as the protein. No protein adsorption by the polymer could be detected.

Example 18

Bed Expansion

In this test, a 40 cm×1 cm column was packed with fluoropolymer particles prepared in the manner of Example 14 and subsequently screened to a 63 to 82 micrometers particle diameter range. Water was pumped up-flow in the column and the bed expansion ration (the ratio of the bed depth at a given flow rate vs. bed depth without flow) He/Ho, measured at various flow rates. The results are summarized in Table 2.

TABLE 2

|  | Flow Rate (cm/h) | | | | |
| --- | --- | --- | --- | --- | --- |
|  | 8 | 25 | 40 | 55 | 68 |
| Bed Expansion ration (He/Ho) | 1.2 | 1.7 | 1.75 | 1.9 | 2.1 |

These data illustrate the advantageous use of the invention particles, which results from their higher density, i.e., 1.2 g/mL versus only 1.09 g/mL for prior art polymeric articles.

Examples 19 to 27

Chemical Stability of the Resin

A series of tests was carried out to determine the chemical stability of the adsorbent resin prepared in the manner of Example 3. For this series, 200 mg of fluoropolymer particles prepared as in Example 14 were soaked in 2 mL of the solvent indicated. Leakage of the Cibacron Blue F3G-A was checked over time by monitoring the supernatant adsorbance at 620 nm. The dye concentrations measured in the supernatant after 37 days are summarized in Table 3.

TABLE 3

|  | SOLVENT (micromol) | DYE CONCENTRATION |
| --- | --- | --- |
| EXAMPLE 19 | 25% aq. Glycerol | 0.008 |
| EXAMPLE 20 | 1% aq. Sodium dodec. Sulfate | 0.008 |
| EXAMPLE 21 | 8 M urea | 0.004 |
| EXAMPLE 22 | 1 M NaSCN | 0.01 |
| EXAMPLE 23 | 5 M HCl | 0.002 |
| EXAMPLE 24 | dimethyl formamide | 0.01 |
| EXAMPLE 25 | Methanol | n.d |
| EXAMPLE 26 | Acetone | n.d |
| EXAMPLE 27 | Water | 0.002 |

Example 28

Use of the Uncoated Polyfluorinated Particles of the Invention for Reverse-phase Chromatography Polymer particles prepared in the manner of Examples 3 and 4 were packed at 1,600 psi into stainless steel columns of 250 cm length and 0.46 cm inside diameter. The slurry solvent was 50/50 by volume methanol/isopropanol. The gradient test mixture solvent was 50/50 by volume acetonitrile/water with 0.1 TFA. The mobile phase was A=water with 0.1% TFA, B-acetonitrile with 0.1% TFA. The test mixture was Vitamin B-12 (1.0 mg), bovine insulin (3.0 mg), ribonuclease A (3.0 mg), human albumin (3.0 mg) and thyroglobulin (3.0 mg). The retention times (minutes) comparing the effectiveness of methacrylic particles with the pentafluorostyrene polymer particles of the invention are set out in Table 4.

TABLE 4

EFFECTIVENESS OF PENTAFLUOROSTYRENE POLYMER AND FLUORINATED METHACRYLIC POLYMER SUBSTRATES IN REVERSE-PHASE CHROMATOGRAPHY

| Solute | Pentafluorostyrene Polymer | Fluorinated Methacrylic Polymer |
|---|---|---|
| | (Retention time, minutes) | |
| Vitamin B-12 | 1.00 | 1.00 |
| Bovine insulin | 1.59 | 1.75 |
| Ribonuclease A | 1.83 | 2.02 |
| Human albumin | 2.08 | 2.32 |
| Thyroglobulin | 2.40 | 2.72 |

Correlation of the data showed that smooth, symmetrical, non-overlapping curves were obtained. The data therefore clearly demonstrate that both the uncoated pentafluorostyrene polymer and the uncoated fluorinated methacrylic polymer particles are effective media for the chromatographic separation of mixtures of materials such as proteins.

Example 29

Using the columns of Example 28 filled with the uncoated polyfluorinated resin particles, the columns were washed with 60 column volumes of 5.0 normal sodium hydroxide solution, followed by 60 column volumes of deionized water. The solutes were then reinjected and the same gradient as resulted in Example 28 was observed. In particular, the caustic-washed resin showed the same retention as the resin that had not undergone such washing, thus illustrating the robustness of the particles.

Example 30
Modification of Synthesis Variables to Produce Polyfluorostyrene Particles of Widely Different Particle Size

TABLE 5

VARIATION OF PROCESS VARIABLES TO MAKE DIVERSE PARTICLE SIZE

| | | |
|---|---|---|
| Particle Size, micrometers | 16 | 120 |
| Reactants | | |
| Deionized water, mL | 660 | 490 |
| Poly(vinyl alcohol), g | 16 | 3.9 |
| Pentafluorostyrene, g | 10 | 39.8 |
| Ethyleneglycol dimethacrylate, g | 14 | 55.7 |
| Dibutyl phthalate, mL | 32 | 127 |
| Azo-bis-isobutyronitrile, g | 0.12 | 0.48 |
| Benzyl peroxide, g | 0.12 | 0.49 |
| Sodium lauryl sulfate, g | 0.06 | None |
| Agitator Speed, RPM | 900 | 395 |

Upon review of the performance characteristics of the adsorbents of the invention and comparison of those characteristics with the properties of other widely used adsorbent materials, it is clear from the data in Table 5 above that the polyfluorinated adsorbents of the invention are uniformly high in all the physical and chemical properties which are vital to their function.

TABLE 6

COMPARISON OF THE INVENTION WITH OTHER COMMERCIAL AVAILABLE CHROMATOGRAPHY SUPPORTS

| Matrix | Chemical Stability (ph) | Mechanical Stability | Permeability To Maccro- | Non-specific Adsorption | Ease of Derivatization | Resistance of 5N NaOH |
|---|---|---|---|---|---|---|
| Agarose | 4–9 | Low | Excellent | Low | Good | Poor |
| Crosslinked | 2–14 | Low | Excellent | Low | Good | poor |
| Crosslinked dextron | 72 | Low | Poor | Low | Good | Poor |
| Crosslinked polyacrylamide | 2–10 | Medium | Poor | Low | Good | Poor |
| Polyacrylamide/ Dextran | 3–11 | Low | Excellent | Medium | Good | Poor |
| Polyacrylamide/ Agarose | 3–10 | Medium | Good | Medium | Good | Poor |
| Crosslinked hydroxyethyl | 1–14 | High | Good | High | Poor | Very poor |
| Methacrylate Silica | 2–9 | High | Good | High | Poor | Very poor |
| Polystyrene/ Divinylbenzene | 1–14 | High | Good | High | Good | Good |
| Polyfluorinated particle of the invention with hydrophilic surface coating | 1–14 | High | Excellent | Low | Excellent | Excellent |

From the data in Table 6, it can readily be seen that the adsorbents of the invention are chemically stable over a very broad pH range and have a high mechanical stability. The invention adsorbents also have excellent permeability to macromolecules and, quite desirably, low non-specific adsorption properties. In addition, the claimed adsorbents have excellent ease of derivatization and excellent resistance to the corrosive effects of 5N NaOH solutions. None of the other well-known adsorbents have such uniformly outstanding performance in all of the listed functionally important properties.

Example 31

Use of the Fluorinated Particles of the Invention in the Separation of Components of Plasmids The plasmid (Amp resistant) transformed host (DHS-alpha) was grown to high density in an enriched medium and the bacterial pellet was subjected to an alkaline lysis procedure. The lysate was filtered and then precipitated with 0.7 volumes of ice cold isopropyl alcohol (IPA) by centrifugation at 8000×g for 45 minutes. The liquid from the centrifugation was used as the sample to be chromatographed.

A Vantage-L series column (4.4 cm id) was packed with an ethanolic slurry containing approximately 90 ml of the particles described in Example 3 (50 μm, surface area of 300/m/gm, non-PVA coated). The column was packed at about 20 ml/min (approximately 80 cm/h linear flow rate) and operated at 16 ml/min. Column effluent was monitored at 260 nm and the absorbance was detected on a chart recorder. The column was equilibrated with EQB (0.1 M potassium phosphate, pH 7, 2 mM tetrabutylammonium-phosphate (TBAP) and 1% ethanol) and the above described sample to be chromatographed (30 mg worth) was not loaded until the pH of the effluent was less than 9. The wash buffer WB1 was 93% sodium chloride/TRIS/EDTA, pH 8, and 7% ethanol. The elution buffers were the following: EL1 (elution buffer 1) was 0.1 M potassium phosphate, 2 mM TBAP, 10% ethanol; EL2 (elution buffer 2) was 0.1 M potassium phosphate, 2 mM TBAP, 12.5% ethanol; and EL3 (elution buffer 3) was 0.1 M potassium phosphate, 2,mM TBAP, 10% ethanol.

Particle Analysis

Sample 1 was collected during the load and re-equilibration step. No DNA was present on particles in the packed column.

Sample 2 was collected while WB1 was passing through the column and contained the bulk of the RNA and a small amount of nicked open circular DNA.

Sample 3 and 4 were collected during WB1. Sample 3 contained a small amount of supercoiled DNA, more nicked/open circular DNA and the last of the RNA. Sample 4 contained a small quantity of DNA. DNA loss may be reduced by cutting back on the ethanolic content of WB1 or increasing the TBAP concentration, the latter of which is preferred since this may still allow species selectivity by ethanol concentration at samples 4, 5 and 7.

Sample 5 (EL1) contained supercoiled DNA and trace amounts of non-supercoiled.

Sample 6 (EL2) contained the bulk of the DNA of which more than 90% was supercoiled.

Sample 7 (EL3) contained the residual DNA of which at least 25% was non-supercoiled.

Example 32

A Porous Copolymer of Divinyl Benzene, Pentafluorostyrene was Prepared in the Following Manner To 490 ml of distilled water was added nitrogen gas over a 30-minute period to purge the oxygen from the water. Polyvinyl alcohol (3.9 g) was added. Pentafluorostyrene (30.9 g), divinylbenzene (55.0 g) and dibutyl phthalate (127 ml) were mixed together. Azo-bis-isobutyronitrile (0.40 g) and benzoyl peroxide (0.30 g) was added to the mixed monomers. The mixture of the monomers and the peroxide catalysts was added to a stirred mixture of the water and PVA. The mixture was heated to 80 C. with agitation of 800 rpm from a motor-driven, stirring paddle. The mixture was allowed to polymerize over a 4-hour period after which the polymerization was considered complete. The polymer particles were separated from the water and washed and dried. The porogen was removed as Example 1. The resulting particles were porous and had particle size of 50 um.

What is claimed is:

1. A process for the preparation of porous spherical particles of fluorinated polymer adsorbent comprising the steps:

(1) forming a water-insoluble solution of organic compounds comprising (a) a monomer selected from $C_{2-4}$ alkylene glycol esters of a $C_{3-6}$ acrylic acid and a divinyl benzene; (b) a polyfluorinated vinyl monomer; (c) a monomer selected from acrylic acid, methacrylic acid and esters thereof; (d) a free radical initiator; and (e) a water-insoluble, organic solvent-soluble porogenic material, the weight ratio of comonomers (a) plus (b) plus (c) to the porogenic material being from 0.5:1 to 2:1;

(2) forming a dilute solution of a dispersing agent in water from which any oxygen has been purged with inert gas;

(3) with agitation and inert gas purging rapidly dispersing the water-insoluble solution of organic compounds from step (1) into the dilute aqueous solution from step (2) and, as necessary, adjusting the temperature of the dispersion to 30–90° C. to initiate copolymerization of the monomers, the level of mixing energy being sufficient to disperse the water-insoluble solution of organic compounds in the solution from step (2) in the form of liquid droplets having an average diameter of no more than 10–300 micrometers, at least 90% of the droplets being within 40% above or below the average mean particle diameter;

(4) continuing the agitation and oxygen purging of the dispersion from step (3) for a time sufficient to effect complete copolymerization of the monomers and particulation of the droplets in the form of finely divided polymer particles by precipitation of the copolymer therein;

(5) separating the finely divided copolymer particles from the polymerization reaction medium;

(6) extracting the porogenic material from the separated copolymer particles of step (5) by washing the particles with inert organic solvent, thereby forming pores within the copolymer; and (7) drying the porous copolymer particles.

2. A process according to claim 1 wherein the $C_{2-4}$ alkylene glycol ester of a $C_{3-6}$ acrylic acid is selected from the group consisting of ethyleneglycol dimethacrylate, 1,3-propyleneglycol dimethacrylate, 1,4-butanediol dimethacrylate, ethyleneglycol itaconate, ethyleneglycol diacrylate, and ethyleneglycol dimaleate.

3. A process according to claim 1 in which the polyfluorinated monomer is perfluorinated.

4. A process according to claim 1 wherein the polyfluorinated monomer is a compound selected from the group consisting of pentafluorostyrenes, bis-hexafluoroisopropyl itaconates, bis-hexafluoroisopropyl maleates, heptadecafluorodecyl acrylates, perfluorooctyl methacrylates, 2,2,3,3-tetrafluoropropyl methacrylates, mono-trifluoroethyl itaconates, 2,2,2-trifluoroethyl maleates, vinyl benzyl perfluoroctanoates and vinyl trifluoroacetates.

5. A process according to claim 1 wherein the monomer (c) of step (1) is one or more compounds selected from the group consisting of acrylic acids, methacrylic acids, methyl-, ethyl-, and hydroxyethyl-esters of acrylic acids or methacrylic acids, epoxide containing esters of acrylic acids or methacrylic acids, and amine esters of acrylic acids or methacrylic acids.

6. A process according to claim 1 wherein the porogenic material is selected from the group consisting of dibutyl phthalate, isopropyl benzene, toluene, 2-methyl-4-pentanone, 2-methyl-4-pentanol, chlorobenzene and mixtures thereof.

7. A process according to claim 1 wherein said process is carried out at a temperature of 70–90° C.

8. A particle made by the process according to claim 1.

9. A particle according to claim 8, said particle being coated with a hydrophilic polymer.

10. A particle according to claim 9, wherein the hydrophilic polymer is poly(vinyl alcohol).

* * * * *